US012653996B2

(12) United States Patent (10) Patent No.: US 12,653,996 B2
Jadhav et al. (45) Date of Patent: Jun. 16, 2026

(54) CONNECTOR COUPLING ASSEMBLY

(71) Applicant: CareFusion 303, Inc., San Diego, CA (US)

(72) Inventors: Amarsinh Deeliprao Jadhav, Bangalore (IN); Anand Viswanathan, Chennai (IN); Kanjimpuredathil Muralikrishna Menon, Bangalore (IN); Rahul Malviya, Salmon Arm (CA); Jason Andrew Wine, Brea, CA (US); Sumit Rajpal, Panipat (IN); Abin Austin, Thrissur (IN); Kaushik Suman, Chaibasa (IN)

(73) Assignee: CAREFUSION 303, INC., San Diego, CA (US)

( * ) Notice: Subject to any disclaimer, the term of this patent is extended or adjusted under 35 U.S.C. 154(b) by 726 days.

(21) Appl. No.: 18/088,491

(22) Filed: Dec. 23, 2022

(65) Prior Publication Data

US 2024/0207594 A1     Jun. 27, 2024

(51) Int. Cl.
    *A61M 39/22*         (2006.01)
    *A61M 39/10*         (2006.01)
(52) U.S. Cl.
    CPC ........ *A61M 39/1011* (2013.01); *A61M 39/22* (2013.01); *A61M 2039/1061* (2013.01)
(58) Field of Classification Search
    CPC .. A61M 39/10; A61M 39/1011; A61M 39/22; A61M 39/26; A61M 2039/1061;
    (Continued)

(56)               References Cited

U.S. PATENT DOCUMENTS 5,713,856  A      2/1998   Eggers et al.
    6,874,522  B2     4/2005   Anderson et al.
                      (Continued)

FOREIGN PATENT DOCUMENTS

EP        1678070 A2    7/2006
    EP        1517723 B1    1/2007
                    (Continued)

OTHER PUBLICATIONS

Bangert, Bill, "Shorter times to blood transfusion associated with decreased death risk in trauma patients", Medical Xpress, Apr. 14, 2016, https://medicalxpress.com/news/2016-04-shorter-blood-transfusion-decreased-death.html.
                      (Continued)

*Primary Examiner* — Laura A Bouchelle
(74) *Attorney, Agent, or Firm* — Maschoff Brennan

(57)               ABSTRACT

A coupler including a first connector having a first end, a second end opposite the first end, and a first valve disposed between the first end and the second end. The first valve having a compressed state and an expanded state. The coupler includes a second connector having a housing, a connecting portion extending from the housing, and a second valve disposed at least partially within the housing, the second valve having a compressed state and an expanded state. The coupler further includes a collar coupled to the housing of the second connector and configured to receive at least a portion of the first connector to detachably couple the first connector to the collar and the second connector such that the housing of the second connector is at least partially disposed within the first connector.

19 Claims, 8 Drawing Sheets

(58) Field of Classification Search
CPC . A61M 2039/1072; F16L 37/28; F16L 37/30;
F16L 37/32; F16L 37/34
See application file for complete search history.

(56) References Cited

U.S. PATENT DOCUMENTS

| | | | |
|---|---|---|---|
| 7,004,934 | B2 | 2/2006 | Vaillancourt |
| 7,040,598 | B2 | 5/2006 | Raybuck |
| 7,153,296 | B2 | 12/2006 | Mitchell |
| 7,350,764 | B2 | 4/2008 | Raybuck |
| 7,396,051 | B2 | 7/2008 | Baldwin et al. |
| 7,763,013 | B2 | 7/2010 | Baldwin et al. |
| 7,766,394 | B2 | 8/2010 | Sage et al. |
| 7,794,675 | B2 | 9/2010 | Lynn |
| 7,803,139 | B2 | 9/2010 | Fangrow, Jr. |
| 7,803,140 | B2 | 9/2010 | Fangrow, Jr. |
| 7,815,614 | B2 | 10/2010 | Fangrow, Jr. |
| 7,918,243 | B2 | 4/2011 | Diodati et al. |
| 7,998,134 | B2 | 8/2011 | Fangrow et al. |
| 8,123,738 | B2 | 2/2012 | Vaillancourt |
| 8,142,418 | B2 | 3/2012 | Mcmichael et al. |
| 8,211,069 | B2 | 7/2012 | Fangrow, Jr. |
| 8,262,628 | B2 | 9/2012 | Fangrow, Jr. |
| 8,361,408 | B2 | 1/2013 | Lynn |
| 8,480,968 | B2 | 7/2013 | Lynn |
| 8,777,908 | B2 | 7/2014 | Fangrow, Jr. |
| 8,777,909 | B2 | 7/2014 | Fangrow, Jr. |
| 8,795,256 | B1 | 8/2014 | Smith |
| 8,888,758 | B2 | 11/2014 | Mansour |
| 8,899,267 | B2 | 12/2014 | Diodati et al. |
| 8,910,919 | B2 | 12/2014 | Bonnal et al. |
| 8,974,425 | B2 | 3/2015 | Tachizaki et al. |
| 8,974,437 | B2 | 3/2015 | Williams et al. |
| 9,114,242 | B2 | 8/2015 | Fangrow et al. |
| 9,126,028 | B2 | 9/2015 | Fangrow et al. |
| 9,126,029 | B2 | 9/2015 | Fangrow et al. |
| 9,192,753 | B2 | 11/2015 | Lopez et al. |
| 9,234,616 | B2 | 1/2016 | Carrez et al. |
| 9,358,379 | B2 | 6/2016 | Fangrow, Jr. |
| 9,433,769 | B2 | 9/2016 | Bayly |
| 9,468,749 | B2 | 10/2016 | Mansour et al. |
| 9,492,649 | B2 | 11/2016 | Carrez et al. |
| 9,636,492 | B2 | 5/2017 | Fangrow, Jr. |
| 9,724,504 | B2 | 8/2017 | Fangrow, Jr. et al. |
| 9,724,505 | B2 | 8/2017 | Williams et al. |
| 9,861,805 | B2 | 1/2018 | Dennis et al. |
| 9,933,094 | B2 | 4/2018 | Fangrow |
| 9,974,939 | B2 | 5/2018 | Fangrow, Jr. |
| 9,974,940 | B2 | 5/2018 | Fangrow, Jr. |
| 10,029,086 | B2 | 7/2018 | Nowak et al. |
| 10,156,306 | B2 | 12/2018 | Fangrow |
| 10,173,045 | B2 | 1/2019 | Mansour |
| 10,179,203 | B1 | 1/2019 | Huslage et al. |
| 10,195,415 | B2 * | 2/2019 | Yeh ..................... A61M 39/26 |
| 10,315,025 | B2 | 6/2019 | Phillips et al. |
| 10,398,887 | B2 | 9/2019 | Fangrow, Jr. et al. |
| 10,441,507 | B2 | 10/2019 | Sanders |
| 10,518,078 | B2 | 12/2019 | Stjernberg Bejhed et al. |
| 10,569,073 | B2 | 2/2020 | Hallisey et al. |
| 10,625,068 | B2 | 4/2020 | Leuthardt et al. |
| 10,655,764 | B2 | 5/2020 | Jones et al. |
| 10,697,570 | B2 | 6/2020 | Fangrow |
| 10,744,315 | B2 | 8/2020 | Sanders |
| 10,842,982 | B2 | 11/2020 | Fangrow, Jr. |
| 10,857,346 | B2 | 12/2020 | Dennis et al. |
| 10,864,362 | B2 | 12/2020 | Jones et al. |
| 10,881,847 | B2 | 1/2021 | Lynn |
| 11,168,818 | B2 | 11/2021 | Fangrow |
| 11,207,514 | B2 | 12/2021 | Kakinoki |
| 11,235,135 | B2 | 2/2022 | Tsai |
| 11,273,297 | B2 | 3/2022 | Kakinoki |
| 11,484,471 | B2 | 11/2022 | Sanders |
| 11,491,084 | B2 | 11/2022 | Ueda et al. |
| 2004/0215158 | A1 | 10/2004 | Anderson |
| 2005/0090805 | A1 | 4/2005 | Shaw et al. |
| 2006/0129109 | A1 | 6/2006 | Shaw et al. |
| 2007/0088292 | A1 | 4/2007 | Fangrow, Jr. |
| 2007/0088293 | A1 | 4/2007 | Fangrow, Jr. |
| 2007/0088294 | A1 | 4/2007 | Fangrow, Jr. |
| 2007/0225635 | A1 | 9/2007 | Lynn |
| 2008/0039803 | A1 | 2/2008 | Lynn |
| 2011/0106046 | A1 | 5/2011 | Hiranuma |
| 2014/0249487 | A1 | 9/2014 | Lynn |
| 2014/0330254 | A1 | 11/2014 | Rosenberger et al. |
| 2016/0000363 | A1 | 1/2016 | Jones et al. |
| 2018/0200147 | A1 | 7/2018 | Sanders |
| 2019/0184152 | A1 | 6/2019 | Kakinoki |
| 2019/0282797 | A1 | 9/2019 | Tsa |
| 2020/0113784 | A1 | 4/2020 | Lopez et al. |
| 2020/0179672 | A1 | 6/2020 | Kakinoki |
| 2020/0215319 | A1 | 7/2020 | Fangrow, Jr. et al. |
| 2020/0284385 | A1 | 9/2020 | Fangrow |
| 2020/0323734 | A1 | 10/2020 | Ueda et al. |
| 2020/0338331 | A1 | 10/2020 | Sanders |
| 2021/0069484 | A1 | 3/2021 | Tsai |
| 2021/0077803 | A1 | 3/2021 | Lynn |
| 2021/0252267 | A1 | 8/2021 | Fangrow, Jr. |
| 2021/0388926 | A1 | 12/2021 | Martin et al. |
| 2021/0393938 | A1 | 12/2021 | Lynn et al. |
| 2022/0260189 | A1 | 8/2022 | Deuse |
| 2022/0282814 | A1 | 9/2022 | Fangrow |
| 2022/0288378 | A1 | 9/2022 | Mermelshtein et al. |

FOREIGN PATENT DOCUMENTS

| | | | |
|---|---|---|---|
| EP | 1622675 | B1 | 8/2009 |
| EP | 2144634 | A1 | 1/2010 |
| EP | 2219721 | B1 | 8/2010 |
| EP | 2298407 | A1 | 3/2011 |
| EP | 2694132 | A1 | 2/2014 |
| EP | 2562456 | B1 | 6/2014 |
| EP | 2782633 | A1 | 10/2014 |
| EP | 1842002 | B1 | 4/2015 |
| EP | 2736582 | B1 | 5/2015 |
| EP | 2089094 | B1 | 1/2016 |
| EP | 2753396 | B1 | 12/2017 |
| EP | 2736584 | B1 | 4/2018 |
| EP | 3305361 | A1 | 4/2018 |
| EP | 2271398 | B1 | 11/2018 |
| EP | 2480281 | B1 | 11/2018 |
| EP | 2790750 | B1 | 11/2018 |
| EP | 2331191 | B1 | 3/2019 |
| EP | 3079756 | B1 | 3/2019 |
| EP | 2121114 | B1 | 5/2019 |
| EP | 2719419 | B1 | 5/2019 |
| EP | 2956204 | B1 | 8/2019 |
| EP | 3421077 | B1 | 8/2019 |
| EP | 3530313 | A1 | 8/2019 |
| EP | 3538201 | A1 | 9/2019 |
| EP | 3570807 | A1 | 11/2019 |
| EP | 3570809 | A1 | 11/2019 |
| EP | 2536463 | B1 | 4/2020 |
| EP | 3381505 | B1 | 5/2020 |
| EP | 3538201 | B1 | 5/2020 |
| EP | 1904152 | B1 | 12/2020 |
| EP | 2150307 | B1 | 12/2020 |
| EP | 3313490 | B1 | 1/2021 |
| EP | 3760275 | A1 | 1/2021 |
| EP | 3851155 | A1 | 7/2021 |
| EP | 3517164 | B1 | 9/2021 |
| EP | 3954355 | A1 | 2/2022 |
| EP | 3960229 | A1 | 3/2022 |
| EP | 3973044 | A1 | 3/2022 |
| EP | 3305361 | B1 | 5/2022 |
| EP | 3134052 | B1 | 8/2022 |
| EP | 3530313 | B1 | 8/2022 |
| WO | WO-2019187839 | A1 | 10/2019 |
| WO | WO-21099437 | A1 | 5/2021 |
| WO | WO-2021099437 | A1 | 5/2021 |
| WO | WO-21180675 | A1 | 9/2021 |
| WO | WO-2021180675 | A1 | 9/2021 |
| WO | WO-21252197 | A1 | 12/2021 |
| WO | WO-2021252197 | A1 | 12/2021 |
| WO | WO-2021263198 | A1 | 12/2021 |

(56)                    References Cited

FOREIGN PATENT DOCUMENTS

| WO | WO-22042956 A1 | 3/2022 |
| WO | WO-2022042956 A1 | 3/2022 |
| WO | WO-22149339 A1 | 7/2022 |
| WO | WO-2022149339 A1 | 7/2022 |
| WO | WO-22207560 A1 | 10/2022 |
| WO | WO-2022207560 A1 | 10/2022 |

OTHER PUBLICATIONS

Icumedical, "ChemoClave™ Needlefree Close System Transfer Device (CSTD)", date unknown, https://www.icumed.com/products/oncology/closed-system-transfer- devices/chemoclave.

Icumedical, "ChemoLock™ Needlefree Closed System Transfer Device (CSTD)", date unknown, https://www.icumed.com/products/oncology/closed-system-transfer-devices/chemolock.

Rickard, et al., "Securing All intraVenous devices Effectively in hospitalised patients—the SAVE trial: study protocol for a multicentre randomised controlled trial", BMJ Open, Sep. 23, 2015;5(9):e008689, doi: 10.1136/bmjopen-2015-008689. PMID: 26399574; Pmcid: PMC4593168.

Tribology, "Coefficient of friction, Rolling resistance and Aerodynamics", date unknown, https://www.tribology-abc.com/abc/cof.htm.

International Search Report and Written Opinion for Application No. PCT/US2023/081003, dated Mar. 12, 2024, 11 pages.

Lineus Medical, SafeBreak Product Features and Benefits Brochure, May 2021, MKG 0058 5/21 Rev. 02.

Przen, "Lineus Medical Goes International, Signs ONEY for Distribution in Korea", PRZen Online Press Release Distribution, PrZen/33448014, MKG-0130 Rev 00, retrieved from the internet https://przen.com/pr/lineus-medical-goes-international-signs-oney-for-distribution-in-korea-przen-33448014 [Last retrieved Jan. 13, 2023].

Ivteam, "Force-activated separation IV connectors", 2022, retrieved from the internet https://www.ivteam.com/intravenous-literature/force-activated-separation-iv-connectors/ [Last retrieved Jan. 13, 2023].

Tada Group Ab, LinkedIn Post "ReLink granted patent in Japan", LinkedIn, Mar. 2022, retrieved from the internet https://se.linkedin.com/company/tadamedical?trk=public_post_reshare_feed-actor-image&original_referer= [Last retrieved Mar. 2022].

* cited by examiner

CONNECTOR COUPLING ASSEMBLY

FIELD OF THE INVENTION

The present disclosure generally relates to connectors, and, in particular, to connector couplings.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. Often, tubing or catheters are coupled or secured to each other to allow fluid communication between various portions of tubing or catheters.

In some applications, such tubing or catheters may become dislodged due to improper securement and/or when the coupling is subject to forces greater than what the coupling is designed to withstand.

SUMMARY

One or more embodiments of the present disclosure are directed to a coupler including a first connector having a first end, a second end opposite the first end, and a first valve disposed between the first end and the second end, the first valve having a compressed state and an expanded state, a second connector having a housing, a connecting portion extending from the housing, and a second valve disposed at least partially within the housing, the second valve having a compressed state and an expanded state, and a collar coupled to the housing of the second connector and configured to receive at least a portion of the first connector to detachably couple the first connector to the collar and the second connector such that the housing of the second connector extends through the first end of the first connector, wherein the first valve and the second valve are in the compressed state when the first connector is coupled to the collar and the collar is coupled to the second connector. The first connector is configured to decouple from the collar and the second connector in response to a pullout force exceeding a predetermined threshold force.

In some embodiments, the collar includes a first collar end and second collar end opposite the first end, the first collar end including an engaging edge extending radially inward from the first collar end and a securing rim disposed at the second collar end. The first connector may be coupled to the first collar end of the collar and the second connector is coupled to the second collar end when the first connector is coupled to the collar and the collar is coupled to the second connector. The engaging edge may engage with a groove disposed on the second end of the first connector to secure the first connector to the collar when the first connector is coupled to the collar.

In some embodiments, the pullout force is a force applied to the first connector along a central axis of the first connector and the central axis extends at least along a length of the first connector. The central axis may extend through the first connector, the collar, and the second connector when the first connector is coupled to the collar and the collar is coupled to the second connector.

In some embodiments, the first connector includes a body configured to compress the second valve when the first connector is coupled to the collar and the collar is coupled to the second connector. The body may at least partially be disposed within the housing when the first connector is coupled to the collar and the collar is coupled to the second connector.

In some embodiments, the second valve is in the expanded state when the first connector is disconnected from the collar.

In some embodiments, the first valve is in the expanded state when the first connector is disconnected from the collar.

In some embodiments, the first connector is configured to remain coupled to the collar when the pullout force does not exceed the predetermined threshold force.

In some embodiments, the first valve does not overlap with the second valve.

In some embodiments, at least a portion of the housing is configured to compress the first valve when the first connector is coupled to the collar and the collar is coupled to the second connector.

In some embodiments, the coupler has a first configuration and in the first configuration the first connector coupled to the collar and the collar is coupled to the second connector such that the first connector is at least partially disposed within the collar and the second connector is at least partially disposed within the first connector.

In some embodiments, the coupler has a second configuration and in the second configuration the first connector is disconnected from the collar and the collar is coupled to the second connector.

In some embodiments, the first connector is coupled to a first portion of tubing at the first end and the second connector is coupled to a second portion of tubing at the connecting portion.

In some embodiments, the second connector includes a distributor and a channel having an inlet, the second valve being coupled to the distributor and the distributor is disposed between the inlet and an opening of the housing.

In some embodiments, a fluid pathway is formed between the connecting portion of the second connector and the first end of the first connector when the first connector is coupled to the collar and the collar is coupled to the second connector.

One or more embodiments of the present disclosure are directed to a coupler including a first connector having a first end, a second end opposite the first end, a body having a channel, and a first valve disposed between the first end and the second end, the first valve having a compressed state and an expanded state, a second connector having a housing, a connecting portion extending from the housing, and a second valve disposed at least partially within the housing, the second valve having a compressed state and an expanded state and the housing having an opening configured to receive a portion of the first connector, and a collar coupled to the housing of the second connector and configured to receive at least a portion of the first connector to detachably couple the first connector to the collar and the second connector such that the housing of the second connector extends through the first end of the first connector, the collar having a first collar end and second collar end opposite the first end, the first collar end including an engaging edge extending radially inward from the first collar end and a securing rim disposed at the second collar end. The first valve and the second valve are in the compressed state when the first connector is coupled to the collar. The first connector is configured to decouple from the collar and the second connector in response to a pullout force exceeding a predetermined threshold force.

One or more embodiments of the present disclosure are directed to a coupler including a first connector having a first end, a second end opposite the first end and including a groove, a body having a channel and a fluid opening, and a first valve disposed between the first end and the second end, the first valve having a compressed state and an expanded state, wherein the fluid opening is fluid communication with the channel, a second connector having a housing, a connecting portion extending from the housing, and a second valve disposed at least partially within the housing, the second valve having a compressed state and an expanded state and the housing having an opening configured to receive a portion of the first connector, wherein the second valve seals the opening when second valve is in the expanded state, and a collar coupled to the housing of the second connector and configured to receive at least a portion of the first connector to detachably couple the first connector to the collar and the second connector such that the housing of the second connector extends through the first end of the first connector, the collar having a first collar end and second collar end opposite the first end, the first collar end including an engaging edge extending radially inward from the first collar end and a securing rim disposed at the second collar end, the engaging edge disposed within the groove when the first connector is coupled to the collar. The first valve and the second valve are in the compressed state when the first connector is coupled to the collar. The first connector is configured to decouple from the collar and the second connector in response to a pullout force exceeding a predetermined threshold force. A fluid pathway is formed between the first end of the first connector and the connecting portion of the second connector and when the first connector is coupled to the collar and the collar is coupled to the second connector.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
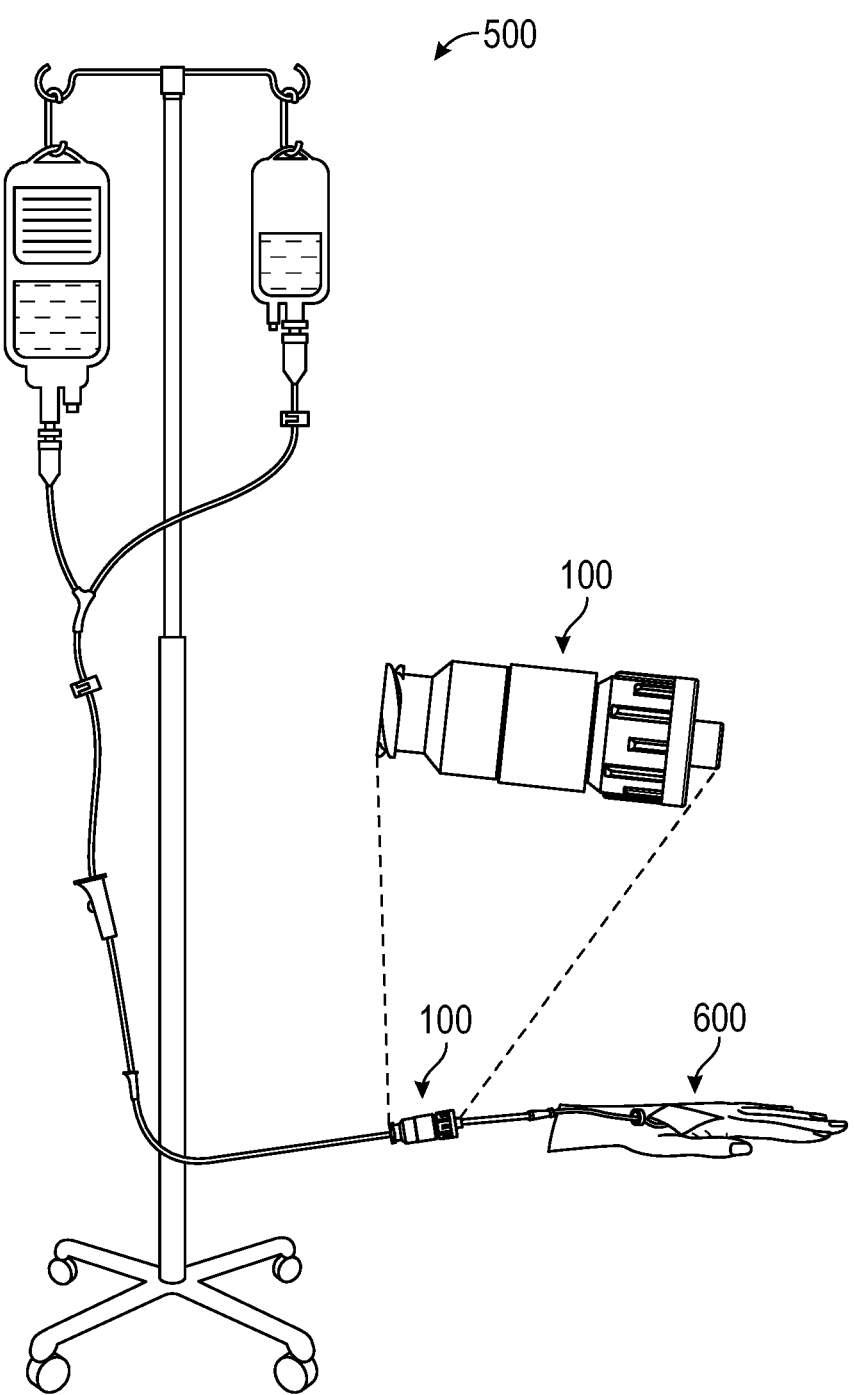
FIG. 1 is a system diagram showing a coupler assembly in use, in accordance with various aspects of the present disclosure.

The disclosed coupler assembly includes a first connector, a collar, and a second connector. The collar is configured to couple the first connector to the second connector. The coupler assembly may have a first configuration and a second configuration. In the first configuration, the first connector is coupled to the collar, and the first connector and the collar are coupled to the second connector. In the second configuration, the first connector is decoupled from the collar, which is coupled to the second connector.

The coupler assembly may be configured to couple a first portion of tubing to a second portion of tubing. For example, the first portion of tubing may be coupled to the first connector and the second portion of tubing may be coupled to the second connector. The first portion of tubing and/or the second portion of tubing may also couple to a patient or fluid source. In some embodiments, the coupler assembly allows for the flow of fluid from the first portion of tubing to the second portion of tubing. For example, the collar may couple the first connector to the second connector such that a fluid pathway is formed through the first connector and the second connector to allow the flow of fluid from the first portion of tubing through the first connector and the second connector to the second portion of tubing. The fluid pathway may allow for the flow of fluid from the second portion of tubing through the second connector and the first connector to the first portion of tubing.

In some embodiments, the collar is configured to allow the first connector to decouple from the second connector. For example, the collar may couple the first connector to the second connector and may be configured to allow the first connector to decouple from the collar and the second connector due to a disconnection event. The collar may allow for one way connection of the first connector to the collar and the second connector. The first connector may be sterilized (e.g., via a sterilized cloth or a sterilizing device) or replaced with a new sterile connector to prevent infection or contamination that can occur if the first connector is re-used without sterilization. In some embodiments, the first connector is configured to decouple based on a force that exceeds a predetermined threshold force. When a force is applied to the first connector, such as a pullout force, that exceeds the predetermined threshold force, the first connector may decouple from the collar and the second connector. The pullout force may be a force that occurs along the longitudinal axis of the first connector. In some embodiments, the pullout force is caused by tugging or pulling on the first portion of tubing coupled to the first connector. Alternatively, the pullout out force applied to the first connector may be caused by tugging or pulling on the second connector and/or the second portion of tubing coupled to the second connector.

In some embodiments, once the first connector is decoupled from the collar and the second connector, the first connector is configured to be re-coupled to the collar. For example, once the first connector decouples from the collar, the first connector may be configured to allow for re-coupling to the collar after a disconnection event.

The detailed description set forth below is intended as a description of various configurations of the subject technol-ogy and is not intended to represent the only configurations in which the subject technology may be practiced. The detailed description includes specific details for the purpose of providing a thorough understanding of the subject tech-nology. However, it will be apparent to those skilled in the art that the subject technology may be practiced without these specific details. In some instances, well-known struc-tures and components are shown in block diagram form in order to avoid obscuring the concepts of the subject tech-nology. Like components are labeled with identical element numbers for ease of understanding. Reference numbers may have letter suffixes appended to indicate separate instances of a common element while being referred to generically by the same number without a suffix letter.

While the following description is directed to the con-nection of medical fittings for the administration of medical fluid using the disclosed coupler, it is to be understood that this description is only an example of usage and does not limit the scope of the claims. Various aspects of the disclosed coupler may be used in any application where it is desirable to secure the connection of various tubing and fittings.

The disclosed coupler assembly overcomes several chal-lenges discovered with respect to certain conventional cou-plers. One challenge with certain conventional couplers is that certain conventional couplers may be improperly secured. Further, during use, certain conventional couplers may be designed to release or dislodge in response to relatively low pullout forces. For example, certain conven-tional couplers may release in response to pullout forces experienced during patients rolling over in bed, patients catching tubing or lines on bed rails, moving patients to a different bed, fidgeting by pediatric patients, and/or disori-ented adult patients pulling out their lines. Indeed, the Association for Vascular Access (AVA) Annual Scientific Meeting in 2017 reported a 10% dislodgement rate for 1,000 patients fitted with peripheral IV catheters, translating to approximately 33 million dislodgements per year in the U.S. alone. Because the accidental or unintentional dislodgement of tubing, catheters, or fittings may interrupt the adminis-tration of medical fluids, the use of certain conventional couplers is undesirable.

Therefore, in accordance with the present disclosure, it is advantageous to provide couplers and coupler/connector assemblies as described herein that allows for improved securement of fittings or connectors. The disclosed couplers and coupler/connector assemblies are structured as described herein so as to permit the secure retention of the first connectors, while allowing for decoupling after a dis-connection event.

Figure 2A:
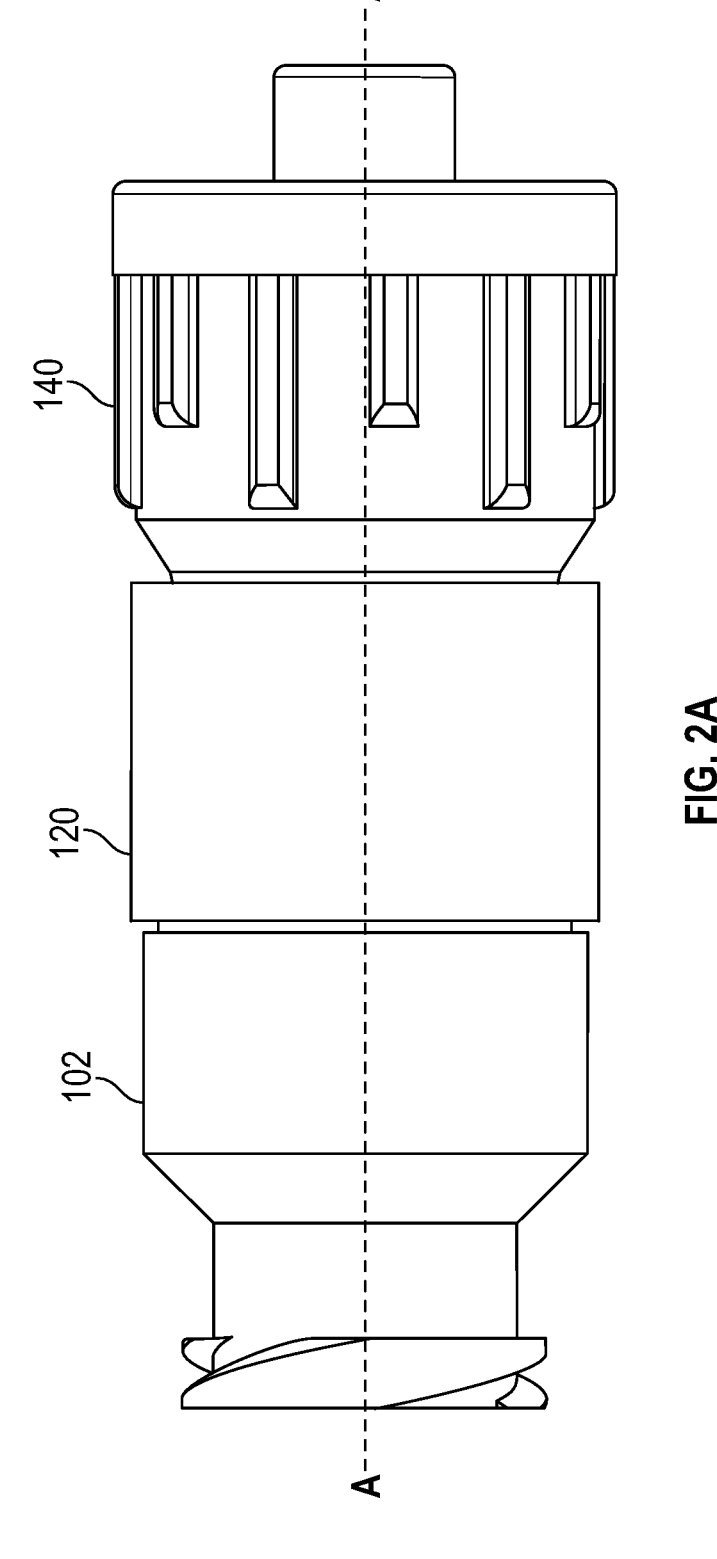
FIG. 2A is a side view of the coupler assembly of FIG. 1, in accordance with various aspects of the present disclosure.
Figures 2B, 2C:
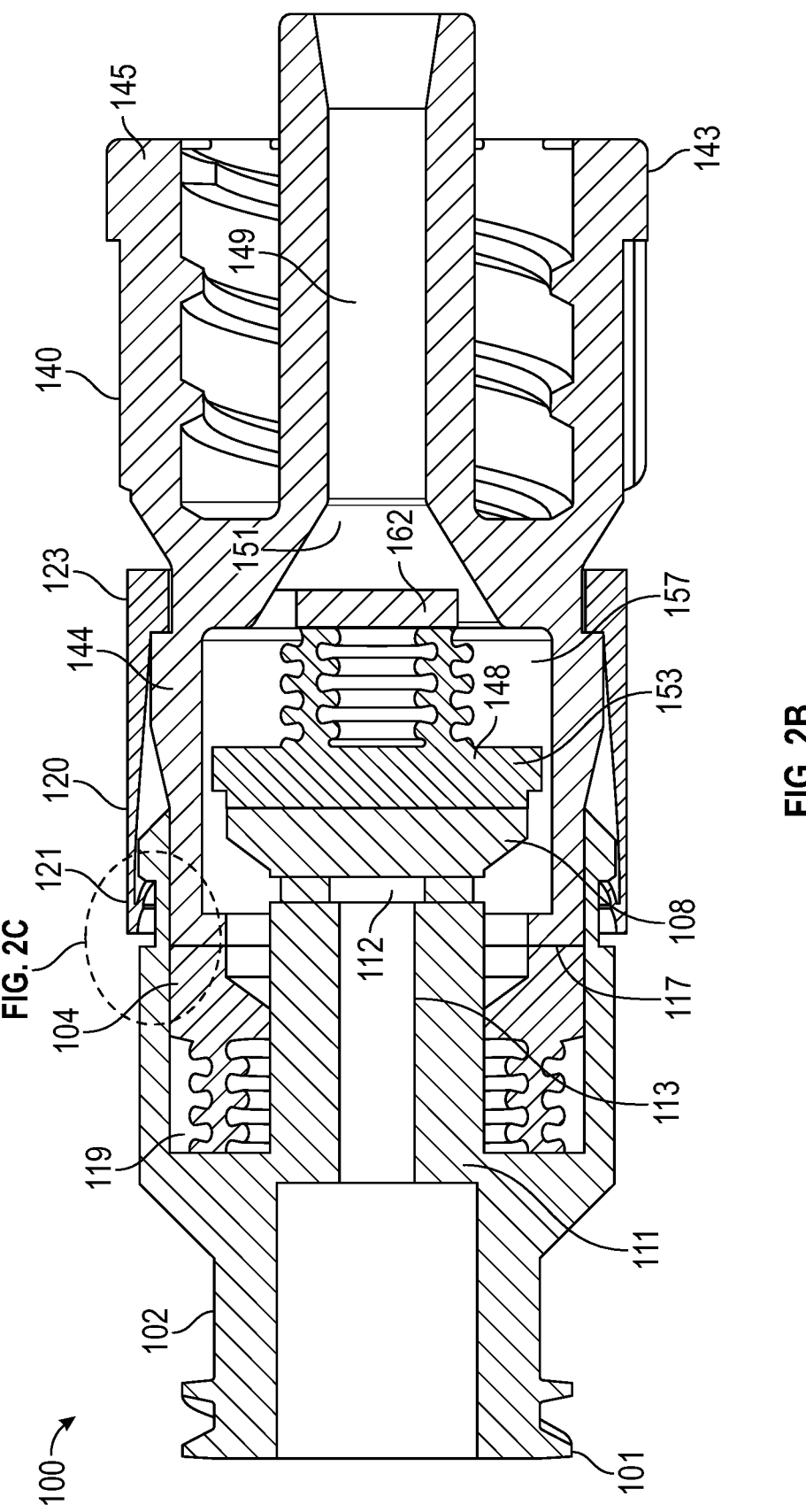
FIG. 2B is a cross sectional side view of the coupler assembly of FIG. 1.
FIG. 2C is a side view of the coupler assembly of FIG. 1 showing a fluid pathway, in accordance with various aspects of the present disclosure.
Figure 2C:
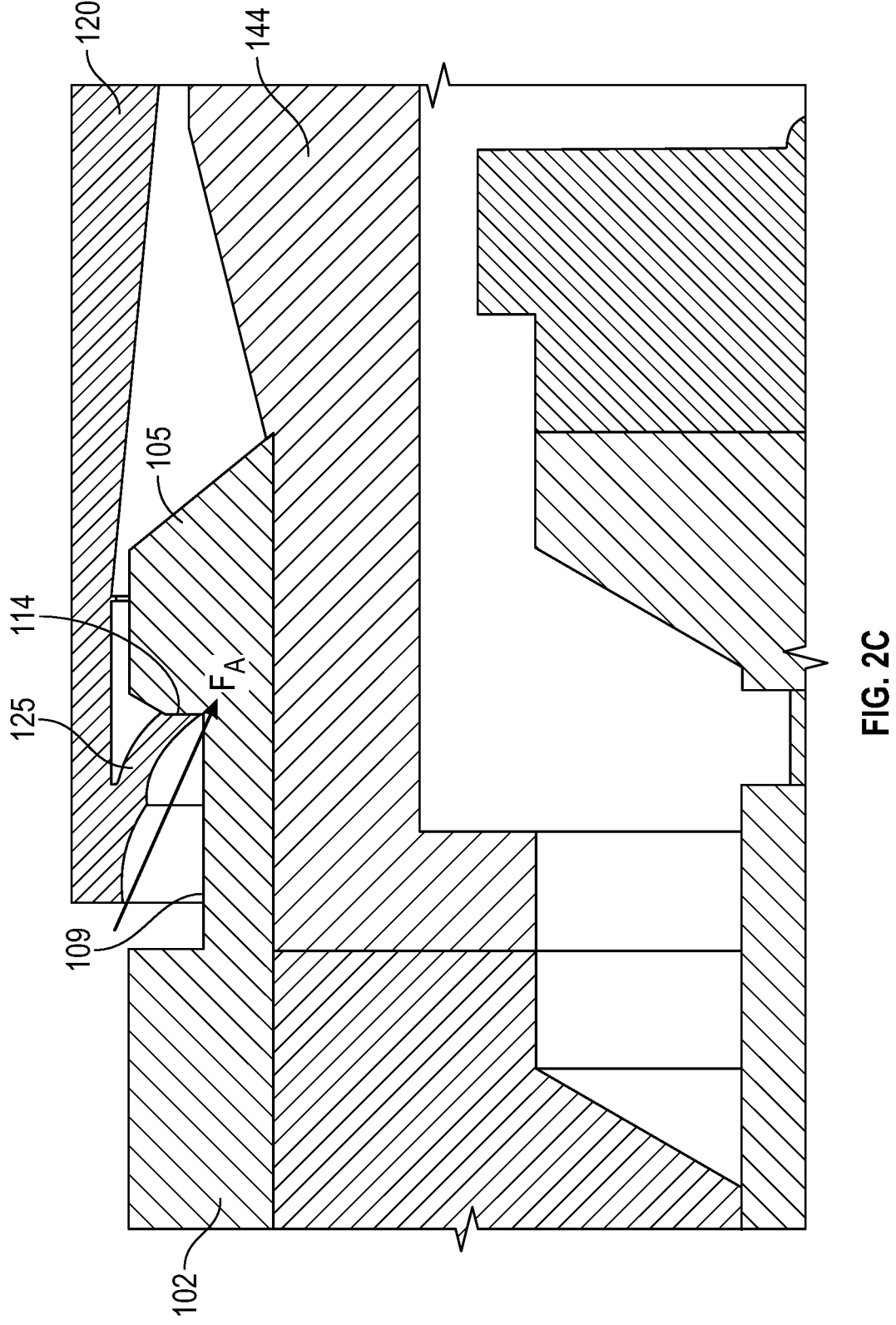
Figure 2D:
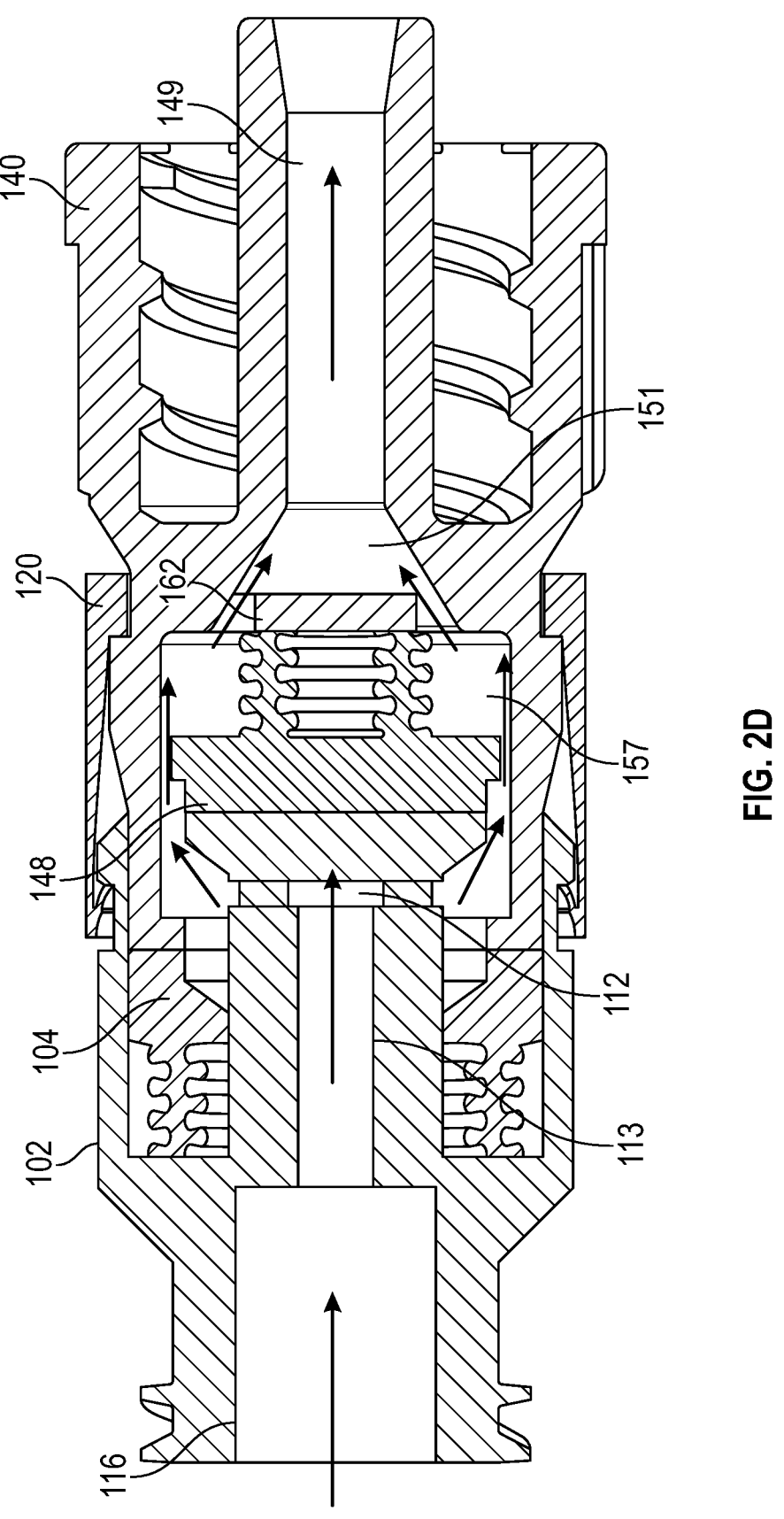
FIG. 2D is zoomed in view of the coupler assembly of FIG. 2B, in accordance with some embodiments of the present disclosure.

FIG. 1 is a system diagram showing a coupler assembly in use, in accordance with various aspects of the present disclosure. FIG. 2A is a side view of the coupler assembly of FIG. 1, in accordance with various aspects of the present disclosure. FIG. 2B is a cross sectional side view of the coupler assembly of FIG. 1. FIG. 2C is a side view of the coupler assembly of FIG. 1 showing a fluid pathway, in accordance with various aspects of the present disclosure. FIG. 2D is zoomed in view of the coupler assembly of FIG. 2B, in accordance with some embodiments of the present disclosure.

Figure 3:
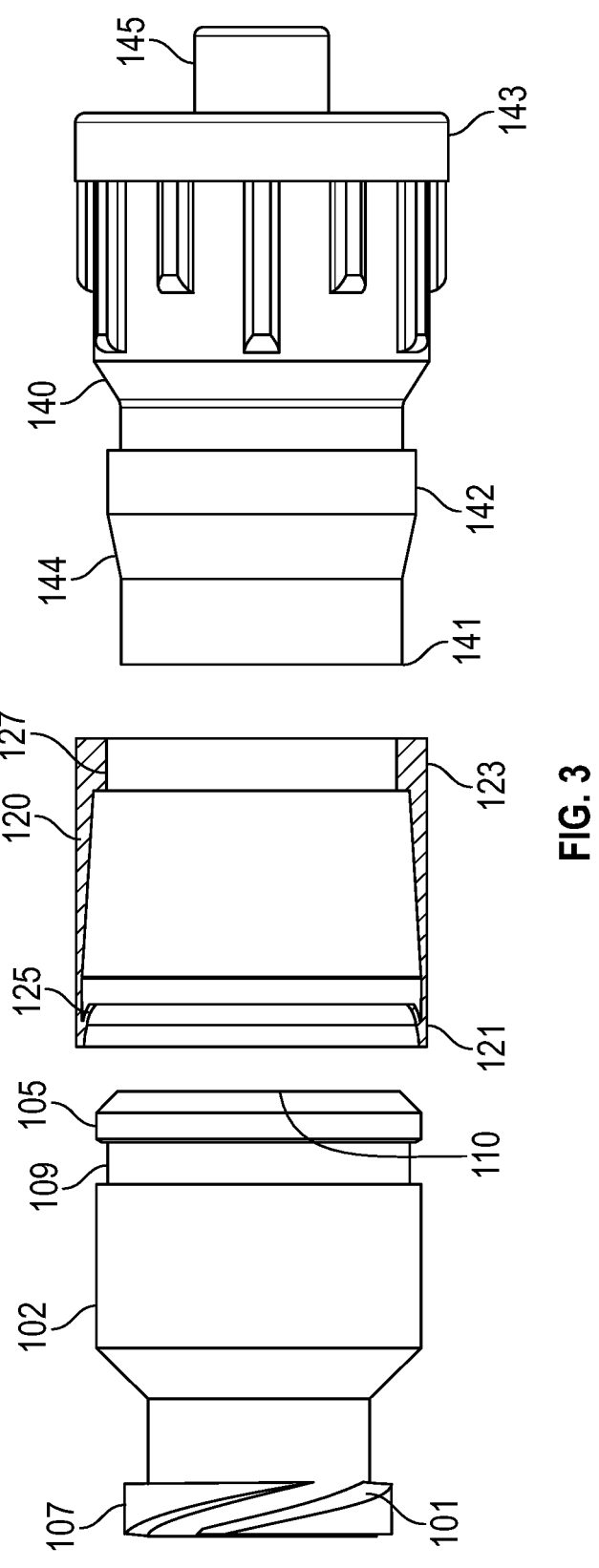
FIG. 3 is an exploded side view of the coupler assembly of FIG. 1 showing a first connector, a collar, and a second connector.
Figure 4A:
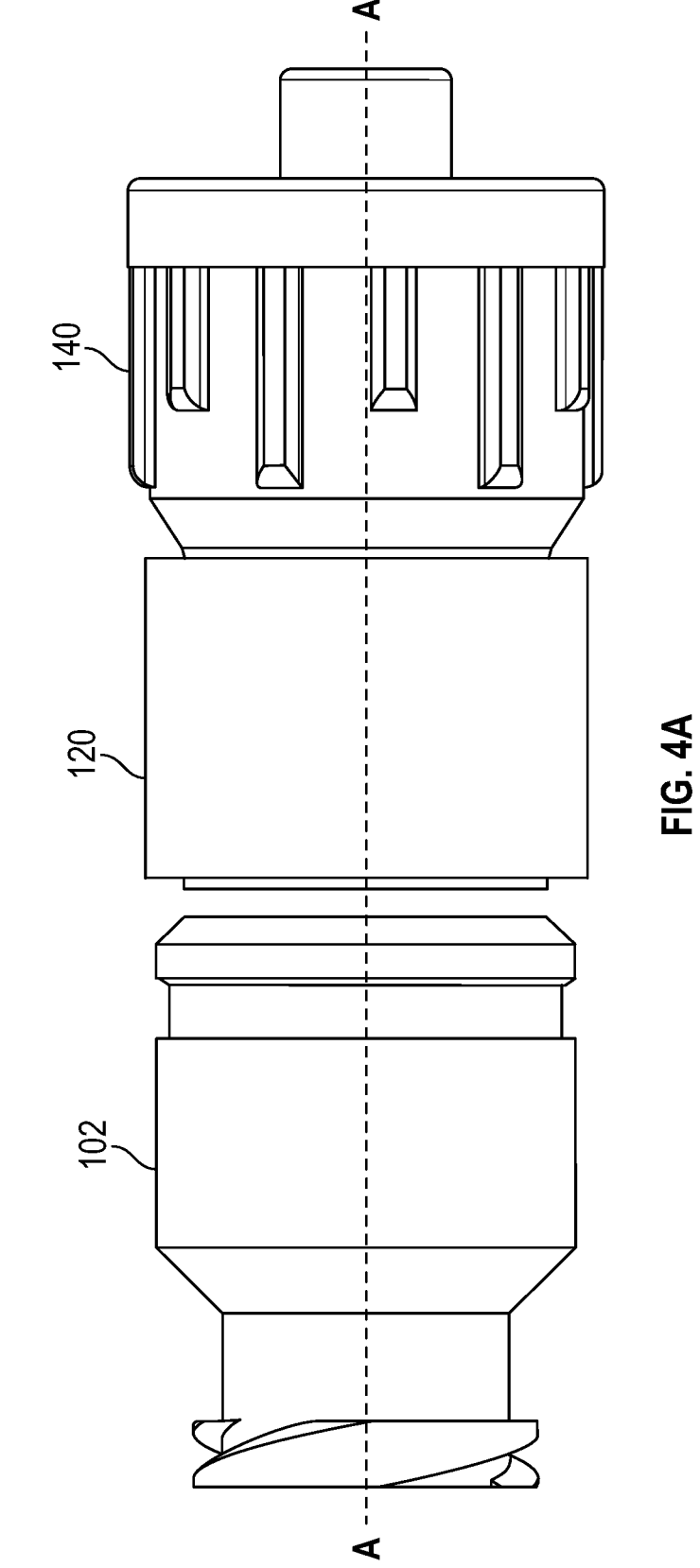
FIG. 4A is a side view of the coupler assembly of FIG. 1 with the collar coupled to the second connector and the collar and second connector decoupled from the first connector, in accordance with some embodiments of the present disclosure.
Figure 4B:
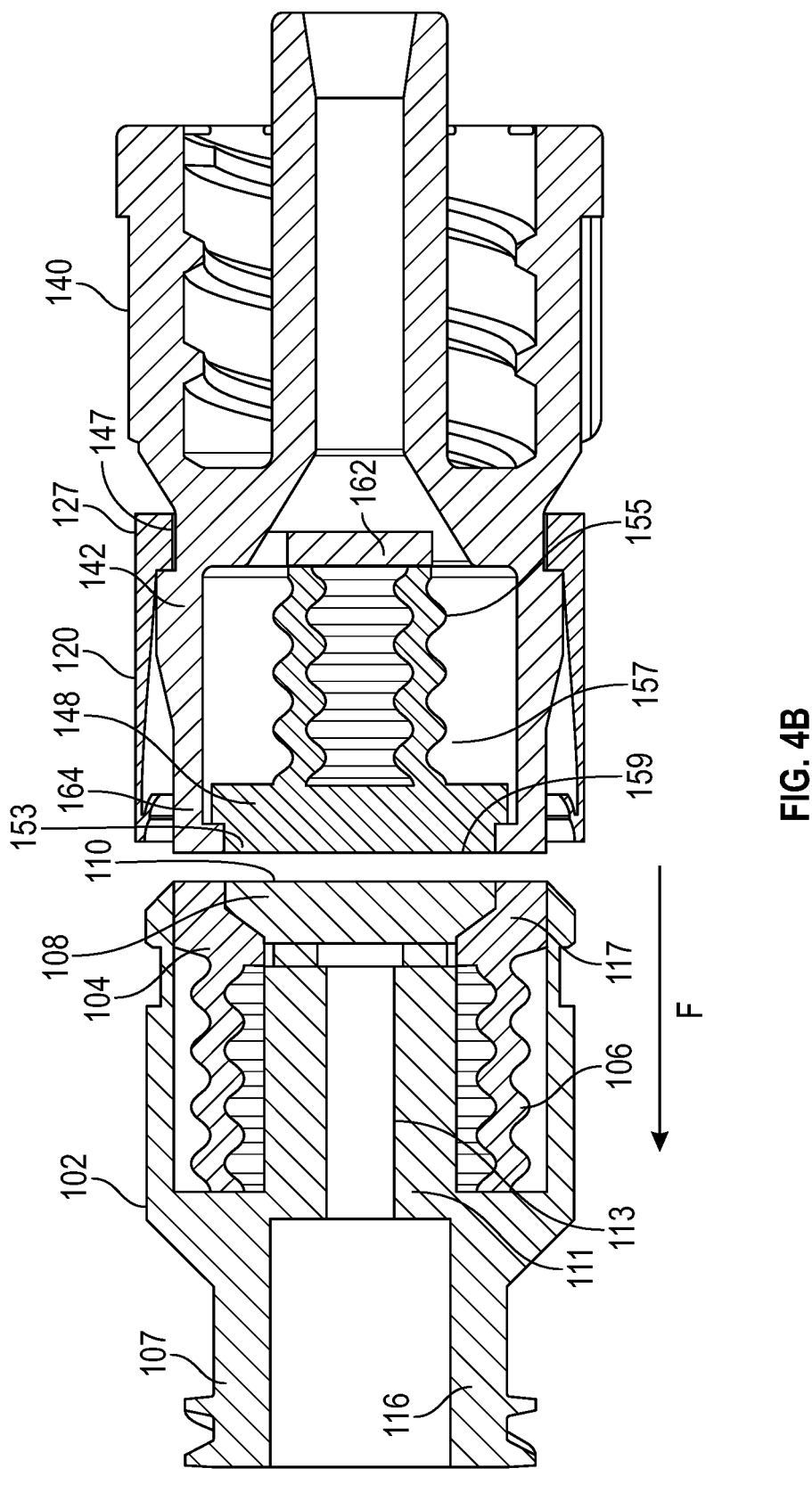
FIG. 4B is a cross sectional side view of the coupler assembly of FIG. 4A.

FIG. 3 is an exploded side view of the coupler assembly of FIG. 1 showing a first connector, a collar, and a second connector. FIG. 4A is a side view of the coupler assembly of FIG. 1 with the collar coupled to the second connector and the collar and second connector decoupled from the first connector, in accordance with some embodiments of the present disclosure. FIG. 4B is a cross sectional side view of the coupler assembly of FIG. 4A.

With reference to FIGS. 1-4B, coupler assembly 100 allows the flow of a fluid, such as a medical fluid, from fluid source 500 to patient end 600 by releasably coupling a portion of tubing or line with another portion of tubing or line in fluid communication. Coupler assembly 100 may include first connector 102, collar 120, and second connector 140. Collar 120 may be configured to couple first connector 102 to second connector 140. In the depicted example, portions of tubing can be terminated with connectors/valves, such as first connector 102 and/or second connector 140. In some embodiments, fluid from fluid source 500 flows through coupler assembly 100 to patient end 600. A cannula or needle may be inserted within a patient at patient end 600 allowing medical fluid to flow from fluid source 500 through coupler assembly 100 and into a patient at patient end 600. In some embodiments, decoupling of first connector 102 from second connector 140 interrupts or prevents flow from fluid source 500 to patient end 600.

In some embodiments, coupler assembly 100 includes central axis A-A and first connector 102, collar 120, and second connector 140 are coupled in series along central axis A-A. First connector 102 and/or second connector 140 may allow for the connection and/or disconnection of tubing to allow for selective fluid communication therebetween. Central axis A-A may extend longitudinally along the length of first connector 102, collar 120, and second connector 140.

In some embodiments, first connector 102 is coupled to second connector 140 via collar 120. Collar 120 may be configured to detachably couple first connector 102 to second connector 140 such that a portion of first connector 102 is disposed within second connector 140. Collar 120 may be configured to allow for one way connection of first connector 102 to collar 120. For example, collar 120 may be configured to prevent re-coupling of first connector 102 to collar 120 once first connector 102 is decoupled from collar 120. Collar 120 may be configured to allow one way connection of first connector 102 to collar 120.

Coupler assembly 100 may have a first configuration (FIGS. 2A-2C) and a second configuration (FIGS. 4A-4B). In the first configuration, first connector 102 is coupled to second connector 140 via collar 120. In the second configu-ration, first connector 102 is decoupled from collar 120, which is coupled to second connector 140. In some embodi-ments, coupler assembly 100 transitions from the first con-figuration to the second configuration in response to a disconnection event. A disconnection even may occur when a pullout force is applied to first connector 102 causing axial movement of first connector 102 relative to collar 120 and second connector 140. In some embodiments, axial move-ment of first connector 102 relative to collar 120 and second connector 140 is caused when the pullout force applied to first connector 102 exceeds a predetermined threshold force.

In some embodiments, first connector 102 is coupled to a first portion of tubing to allow the first portion of tubing to be connected and/or disconnected with second connector 140. First connector 102 may include first end 101 and second end 103. First end 101 may be coupled to tubing (e.g., a first portion of tubing) and second end 103 may be configured to couple to collar 120. In some embodiments, a portion of tubing can be coupled with, or engage with first end 101 of first connector 102. First connector 102 via first end 101 may be in fluid communication with the tubing to allow fluid to pass through first connector 102. In some embodiments, first end 101 can have a flat surface to allow for clinicians to easily clean and disinfect first end 101. First end 101 may be in fluid connection with second end 103. First end 101 and second end 103 may be disposed along the longitudinal length of first connector 102. For example, first end 101 and second 103 may be disposed along central axis A-A. First end 101 and/or second end 103 may include an opening to allow first end 101 and/or second end 103 to be in fluid communication with one or more elements (e.g., tubing, connectors, valves, collars, attachments, etc.). For example, first end 101 may be coupled to a tube and second end 103 may include opening 110 to allow for fluid communication through first connector 102. In some embodiments, first connector 102 includes valve 104, which is configured to be at least partially disposed within opening 110.

In some embodiments, fluid can exit or flow through first connector 102 via second end 103 disposed opposite to first end 101. The flow path through first connector 102 can have a straight fluid pathway to make flushing easier and to reduce the risk of hemolysis. Optionally, first connector 102 can include features (e.g., raised features, gripping features) disposed on the outer surface of first connector 102 to allow a clinician to more easily handle or manipulate first connector 102. Some embodiments of first connector 102 may provide connectors that are compatible with connectors of other portions of fluid delivery systems. First connector 102 may be substantially cylindrically shaped.

In some embodiments, first connector 102 tubing portion 107 disposed at first end 101 and mating portion 105 disposed at second end 103. Tubing portion 107 may be configured to couple to a portion of tubing allowing first connector 102 to be in fluid communication with the portion of tubing. For example, tubing portion 107 may include channel 116 to allow for the flow of fluid within tubing portion 107. Channel 116 may be disposed within tubing portion 107 and extend the length of tubing portion 107.

In some embodiments, mating portion 105 is disposed opposite tubing portion 107 and collar 120 is configured to couple to mating portion 105 to secure first connector 102 to second connector 140. For exampling mating portion 105 may include groove 109 configured to receive a portion of collar 120 to secure collar 120 to first connector 102 and thus couple first connector 102 to second connector 140, as described below. Groove 109 may be disposed on mating portion 105 proximate second end 103. In some embodiments, groove 109 is configured to receive and engage with a portion of collar 120 to secure first connector 102 to collar 120.

In some embodiments, first connector 102 includes body 111 and valve 104. Body 111 may extend from tubing portion 107. For example, body 111 may extend away from tubing portion 107 towards second end 103. In some embodiments, body 111 and tubing portion 107 are formed of a unitary structure. Alternatively, body 111 may be fixedly or removably coupled to tubing portion 107. In some embodiments, body 111 includes channel 113. Channel 113 may be disposed within body 111 and may be in fluid communication with channel 116 of tubing portion 107. For example, tubing portion 107 may be coupled to fluid source 500 via a portion of tubing allowing fluid to flow from fluid source 500 and into channel 116. Fluid may flow from channel 116 into channel 113 of body 111.

First connector 102 may include interior cavity 119, which is the space between body 111 and mating portion 105. For example, mating portion 105 may be a cylinder extending from tubing portion 107 and body 111 may be disposed within mating portion 105. Cavity 119 may be space between an external surface of body 111 and an internal surface of mating portion 105.

Body 111 may include coupling face 108 disposed at an end of body 111 and fluid opening 112 disposed between body 111 and coupling face 108. For example, coupling face 108 may be disposed proximate second end 103 and fluid opening 112 may be disposed between body 111 and second end 103. In some embodiments, fluid opening 112 is in fluid communication with channel 113 and allows fluid within channel 113 to flow through fluid opening 112. Coupling face 108 may be at least partially disposed within opening 110.

In some embodiments, body 111 includes valve 104. Valve 104 may include biasing element 106 and distal end 117. Valve 104 may be disposed between tubing portion 107 and second end 103. In some embodiments, body 111 is disposed within valve 104. For example, body 111 may at least partially extend through valve 104. In some embodiments, valve 104 surrounds body 111.

Biasing element 106 may be coupled to distal end 117. In some embodiments, distal end 117 is disposed proximate second end 103 and biasing element 106 is disposed proximate first end 101 compared to distal end 117. Biasing element 106 may be configured to allow valve 104 to compress and expand. For example, valve 104 may be configured to compress (e.g., shorten in length) or expand (e.g., increase in length). Biasing element 106 may be a spring or spring-like structure allowing valve 104 to be in a compressed state (FIG. 2B) or an expanded state (FIG. 4B). In some embodiments, biasing element 106 couples valve 104 to tubing portion 107 such that when an axial force is applied to valve 104 towards first end 101, valve 104 compresses (e.g., transitions to the compressed state).

In some embodiments, valve 104 is biased to be in an expanded state such that valve 104 is at least partially disposed within opening 110. In the expanded state, distal end 117 of valve 104 may be disposed at second end 103 and at least partially within opening 110. In some embodiments, distal end 117 is configured to surround coupling face 108 when valve 104 is in the expanded state resulting in opening 110 being substantially fluid tight. For example, when valve 104 is in the expanded state, distal end 117 at least partially blocks fluid opening 112 thereby preventing fluid from exiting fluid opening 112.

In some embodiments, when valve 104 is in a compressed state, valve 104 (e.g., distal end 117) may no longer block fluid opening 112 allowing fluid to flow from channel 113 through fluid opening 112. In the compressed state, valve 104 may be disposed between first end 101 and second end 103. For example, in the compressed state, valve 104 may have a length less than the length of valve 104 when valve 104 is in the expanded state. In some embodiments, when valve 104 is in the compressed state, distal end 117 is disposed between tubing portion 107 and fluid opening 112. In the compressed state, distal end 117 allows fluid to exit body 111 via fluid opening 112 but prevents back flow or buildup of fluid. For example, distal end 117 may surround a portion of body 111 between fluid opening 112 and where body 111 extends from tubing portion 107. Distal end 117 may be configured to surround body 111 to prevent liquid from flowing past distal end 117 into cavity 119.

In some embodiments, a second portion of tubing is terminated by second connector 140 to allow the second portion of tubing to be connected and/or disconnected from first connector 102 via collar 120. Second connector 140 may include first end 141 and second end 143 disposed opposite first end 141. First end 141 may include housing 144 and second end 143 may include connecting portion 145, which may be disposed opposite housing 144. In some embodiments, a portion of tubing is coupled with, or engage with connecting portion 145 of second connector 140. In some embodiments, connecting portion 145 includes a threaded connection to facilitate coupling with tubing. For example, connecting portion 145 may include connecting portion 145 configured to couple to a portion of tubing.

In some embodiments, housing 144 includes features (e.g., threads) that allow for second connector 140 to mate with collar 120. Housing 144 may fit together or otherwise engage with second end 123 of collar 120 to allow fluid communication between first connector 102 and second connector 140 and the portions of tubing coupled thereto when first connector 102 is coupled to collar 120. As can be appreciated, first connector 102 and second connector 140 can be coupled and decoupled via collar 120 to permit fluid communication as desired. First connector 102 may detachably couple with second connector 140 via collar 120 to provide needle free connections. Advantageously, first connector 102 may pair with second connector 140 via collar 120 to form a leak-free closed system, allowing the delivery of various drugs or fluids.

In some embodiments, second connector 140 includes connecting portion 145 disposed opposite housing 144. Housing 144 may extend from connecting portion 145. Connecting portion 145 may include channel 149 disposed within connecting portion 145. Channel 149 may include inlet 151, which may be disposed between first end 141 and second end 143. In some embodiments, inlet 151 has a maximum width (e.g., diameter) greater than a maximum width (e.g., diameter) of channel 149. Inlet 151 may be in fluid communication with channel 149 such that liquid entering inlet 151 flows into channel 149 and through tubing portion 145.

Connecting portion 145 may be configured to couple to a portion of tubing (e.g., tubing coupled to patient end 600) such that channel 149 is in fluid communication with the portion of tubing. In some embodiments, an internal surface of connecting portion 145 includes threads to couple or mate with the portion of tubing to allow second connector 140 to be in fluid communication with a portion of tubing.

Housing 144 may extend from connecting portion 145 towards first end 141. Housing 144 may include cavity 157 disposed within housing 144. Cavity 157 may be interior space within housing 144. Housing 144 may include distal end 164 and distal end 164 may include opening 159. In some embodiments, housing 144 includes tapered portion 142 disposed between connecting portion 145 and first end 141 (e.g., opening 159). Tapered portion 142 may be configured to secure collar 120 to second connector 140, as described below.

In some embodiments, second connector 140 includes distributor 162. Distributor 162 may be disposed proximate channel 149. For example, distributor 162 may be disposed at the opening of channel 149. In some embodiments, distributor 162 is disposed at or proximate the location where housing 144 extends from connecting portion 145. Distributor 162 may be at least partially disposed within inlet 151. In some embodiments, distributor 162 is disposed within or proximate inlet 151. Distributor 162 may cause fluid entering inlet 151 to divert around distributor 162 prior to entering inlet 151 and flowing through channel 149. In some embodiments distributor 162 couples to and extends from a portion of housing 144. For example, is some embodiments, distributor 162 is integrally formed with housing 144 and includes apertures or passageways that permit fluid to flow past the distributor through the inlet 151.

In some embodiments, second connector 140 includes valve 148. Valve 148 may include biasing element 155 and distal end 153. Valve 148 may be disposed between distributor 162 and first end 141. In some embodiments, valve 148 is disposed within cavity 157. For example, valve 148 may be housed within cavity 157.

Biasing element 155 may be coupled to distal end 153. In some embodiments, distal end 153 is disposed proximate second end 143 and biasing element 155 is disposed proximate first end 141 compared to distal end 153. Biasing element 155 may be configured to allow valve 148 to compress and expand. For example, valve 148 may be configured to compress (e.g., shorten in length) or expand (e.g., increase in length). Biasing element 155 may be a spring or spring-like structure allowing valve 148 to be in a compressed state (FIG. 2B) or an expanded state (FIG. 4B). In some embodiments, biasing element 155 couples valve 148 to distributor 162 such that when an axial force is applied to valve 148 towards first end second end 143, valve 148 compresses (e.g., transitions to the compressed state).

In some embodiments, valve 148 is biased to be in an expanded state such that valve 148 is at least partially disposed within opening 159. In the expanded state, distal end 153 of valve 148 may be disposed at second end 143 and at least partially within opening 159. In some embodiments, distal end 153 is configured to seal opening 159 when valve 148 is in the expanded state resulting in opening 159 being substantially fluid tight. For example, when valve 148 is in the expanded state, distal end 153 at least partially blocks opening 159 thereby preventing fluid from entering or exiting via opening 159.

In some embodiments, when valve 148 is in a compressed state, valve 148 (e.g., distal end 153) may no longer block opening 159 allowing fluid to flow into opening 159. Fluid may flow into opening 159 and flow through cavity 157, around distributor 162 and into channel 149. In the compressed state, valve 148 may be disposed between opening 159 and distributor 162. For example, in the compressed state, valve 148 may have a length less than the length of valve 148 when valve 148 is in the expanded state. In some embodiments, when valve 148 is in the compressed state, distal end 153 is disposed between opening 159 and distributor 162 such that distal end 153 is disposed within cavity 157. In the compressed state, distal end 153 allows fluid to enter or exit housing 144 (e.g., cavity 157) via opening 159. When valve 148 is in the compressed state, fluid may be allowed to flow from opening 159, through cavity 157, around distributor 162, and into channel 149.

Referring to FIGS. 2A-2D, when first connector 102 is coupled to second connector 140 via collar 120, coupling face 108 of first connector 102 may apply an axial force on valve 148, causing valve 148 to be in the compressed state. Further, coupling of first connector 102 to second connector 140 may cause distal end 164 to apply an axial force on valve 104, causing valve 104 to be in the compressed state. In some embodiments, when first connector 102 is coupled to second connector 140 via collar 120, at least a portion of second connector 102 is disposed within first connector 102.

Valve 104 and valve 148 being in a compressed state when first connector 102 is coupled to second connector 140 via collar 120 results in a fluid pathway (see FIG. 2D) being formed between first connector 102 and second connector 140. For example, distal end 164 may abut valve 104 causing valve 104 to be in the compressed state and causing distal end 164 to be disposed within first connector 102 (e.g., cavity 119). Simultaneously, coupling face 108 may abut valve 148 cause valve 148 to be in the compressed state and causing coupling face 108 to be disposed within second connector 140 (e.g., cavity 157). This results in fluid opening 112 being in fluid communication with cavity 157.

Referring to FIG. 2D, a fluid pathway is formed when coupler assembly 100 is in the first configuration (e.g., when first connector 102 is coupled to second connector 140 via collar 120). In the first configuration, fluid may flow into first connector 102 via channel 116 and into body 111. Fluid may then flow within channel 113 of body 111 and through fluid opening 112 into cavity 157. The fluid may then flow around valve 148 and distributor 162 into inlet 151 and through channel 149, out of second connector 140.

Referring to FIGS. 2A-4B, second connector 140 may be coupled to first connector 102 via collar 120. Collar 120 may include first end or first collar end 121 and second end or second collar end 123. First end 121 of collar 120 may be configured to couple to first connector 102 and second end 123 of collar 120 may be configured to couple to second connector 140. In some embodiments, first end 121 of collar 120 couples to second end 103 of first connector 102 and second end 123 of collar 120 couples to first end 141 of second connector 140. Second end 123 of collar 120 may be configured to couple to housing 144 of second connector 140. Collar 120 may be comprised of a flexible or semi-flexible material. For example, collars 120 may be comprised of rubber. In some embodiments, at least a portion of collar 120 is comprised of a flexible material.

In some embodiments, collar 120 includes securing rim 127, which is configured to engaged with tapered portion 142. Securing rim 127 may be dispose at or proximate second end 123. Tapered portion 142 may include groove 147 configured to engaged with securing rim 127. In some embodiments, collar 120 may be secured to second connector 140 by inserting second connector 140 through collar 120 such that securing rim 127 engages with tapered portion 142. Collar 120 may be secured to second connector 140 by axial moving collar 120 towards second end 143 of second connector 140 until securing rim 127 is disposed with groove 147. Once securing rim 127 is disposed within groove 147, collar 120 is secured to second connector 140. In some embodiments, groove 147 receiving securing rim 127 results in collar 120 being prevented from axially moving along central axis A-A relative to second connector 140.

Referring to FIGS. 2A-3, collar 120 may include engaging edge 125. Engaging edge 125 may be disposed at or proximate first end 121. Engaging edge 125 may extend from first end 121 radially inwards. In some embodiments, engaging edge 125 is a barb-like rubber edge angled towards second end 123 to allow for one way insertion of first connector 102. For example, first connector 102 may be inserted into collar 120, which may be coupled to second connector 140 (e.g., via securing rim 127 and groove 147). Upon insertion of first connector 102 into collar 120, engaging edge 125 may engage with groove 109. In some embodiments, first connector 102 is coupled to collar 120 by disposing engaging edge 125 within groove 109 of mating portion 105. Engaging edge 125 being angled radially inwards allows for axial movement of first connector 102 relative to collar 120 towards second end 123 of collar 120 until engaging edge 125 is disposed within groove 109. Engaging edge 125 being angled radially inwards may also limit axial movement of first connector 102 relative to collar 120 towards first end 121 once first connector 102 is coupled to collar 120. In some embodiments, engaging edge 125 being disposed within groove 109 causes collar 120 (e.g., engaging edge 125) to apply a radially inward force (e.g., force $F_A$) on mating portion 105 (e.g., groove 109 and/or sidewall 114).

Referring to FIGS. 2A-2D, coupler assembly 100 is in the first configuration when second connector 140 is coupled to collar 120 by securing rim 127 within groove 147 and when first connector 102 is coupled to collar 120 and second connector 140 by securing engaging edge 125 within groove 109. Engaging edge 125 may be disposed within groove 109 and abut sidewall 114, which prevents axial movement of first connector 102 relative to collar 120. Engaging edge 125 abutting sidewall 114 may prevent axial movement of first connector 102 away from collar 120.

In some embodiments, in the first configuration, valve 104 applies an axial force on housing 144 and valve 148 applies an axial force on coupling face 108 resulting in first connector 102 and second connector 140 being biased to decouple. Collar 120 being coupled to second connector 140 and first connector 102 may counteract the biasing by preventing axial movement of second connector 140 and first connector 102 relative to collar 120.

Referring to FIGS. 4A-4B, coupler assembly 100 may be configured to be in a second configuration. In the second configuration, first connector 102 is decoupled from collar 120 and collar 120 remains coupled to second connector 140. In the second configuration, valve 104 and valve 148 return to their biased expanded state and the fluid pathway between first connector 102 and second connector 140 is interrupted. In some embodiments, valve 104 returning to the expanded state results in opening 110 being sealed and prevent flow of fluid in/out of first connector 102. In some embodiments, valve 148 returning to the expanded state results in opening 159 being sealed by valve 148 (e.g., distal end 153), preventing flow of fluid in/out of second connector 140. In the second configuration, collar 120 may be coupled to second connector 140 due to securing rim 127 being disposed within groove 147 thereby preventing axial movement of second connector 140 relative to collar 120. Coupler assembly 100 may transition from the first configuration to the second configuration by first connector 102 decoupling from collar 120 when collar 120 is coupled to second connector 140.

In some embodiments, first connector 102 is secured to second connector 140 via collar 120 and first connector 102 is configured to decouple from collar 120. In some embodiments, first connector 102 is configured to decouple from collar 120 due to a disconnection event, which is caused by a pullout force. For example, a pullout force (e.g., force F) may be applied to first connector 102, either by being directly applied to first connector 102 or indirectly applied to first connector 102, such as being applied to tubing coupled to first connector 102. The pullout force may cause first connector 102 to move axially away from collar 120 and second connector 140 along central axis A-A thereby decoupling first connector 102 from collar 120 and second connector 140.

In some embodiments, first connector 102 is decoupled from collar 120 and thus second connector 140 when force F exceeds a predetermined threshold force. For example, if force F is less than the predetermined threshold force, first connector 102 may not decouple from collar 120 and second connector 140. The predetermined threshold force prevents inadvertent or accidental decoupling based on minor forces or movements. The predetermined threshold force may be based on the flexibility and/or stiffness of engaging edge 125. For example, the higher the stiffness of engaging edge 125, the higher the predetermined threshold force. In some embodiments, when the pullout force exceeds the predetermined threshold force, the engaging edge 125 may fail by breakage or the edge 125 can be temporarily or permanently bent backward toward the first connector 102 to then permit decoupling of the first connector 102 from the collar 120.

In some embodiments, the predetermined threshold force is approximately 4 pounds (lbs). The predetermined threshold force may be from approximately 1 lb to approximately 8 lbs, approximately 3 lbs to approximately 7 lbs, approximately 4 lbs to approximately 6 lbs, or greater than 8 lbs. For example, a patient may have a needle/catheter inserted into their skin and the needle/catheter may be coupled to first connector 102 or second connector 140. The patient may walk away from an infusion pump or accidental pull on a fluid line coupled to first connector 102 or second connector 140 and the force exceeds 4 lbs, first connector 102 may automatically release or decouple from collar 120, effectively closing the fluid pathway between first connector 102 and second connector 140, as described herein.

When first connector 102 decouples from collar 120 due to the disconnection event, collar 120 may remain secured and coupled to second connector 140. First connector 102 may decouple from collar 120 in response to force F exceeding a predetermined threshold force. When force F exceeds the predetermined threshold force, sidewall 114 pushes against engaging edge 125, overcoming force $F_A$ and causing first end 121 (e.g., engaging edge 125) to deflect radially outward and becoming displaced from groove 109. For example, in response to the pullout force (e.g., axial force F) exceeding the predetermined threshold force, first connector 102 may axially move relative to collar 120 such that $F_A$ is overcome and first end 121 radially deflects outward and out of groove 109 resulting in collar 120 no longer being secured to first connector 102.

In some embodiments, collar 120 does not include engaging edge 125. Collar 120 may be configured to couple to first connector 102 and prevent first connector 102 from decoupling when force F is less than the predetermined threshold force. For example, collar 120 may include a compressible material that abuts or engages groove 109 causing the compressible material to be disposed within groove 109. The compressible material may be configured exert a compression force groove 109, thereby securing first connector 102 in place and to collar 120. In response to force F exceeding the predetermined threshold force, the compressible material may be configured to compress mating portion 105 to slide out of collar 120 and allowing first connector 102 to decouple from collar 120.

In some embodiments, upon decoupling of first connector 102 from collar 120 and second connector 140, a user sterilizes first connector 102 and recouples first connector 102 to collar 120. In some embodiments, a user may sterilize first connector 102, second connector 140, and/or collar 120. First connector 102 may be recoupled to collar 120 by inserting first connector 102 into collar 120 such that second connector 140 is disposed within first connector 102. First connector 102 may be axially moved relative to collar 120 to couple first connector 102 to collar 120 and second connector 140 by engaging groove 109 with engaging edge 125 thereby securing collar 120 to first connector 102 and securing first connector 102 to second connector 140. Recoupling first connector 102 to collar 120 results in coupler assembly 100 transitioning from the second configuration to the first configuration.

The disclosures described herein include at least the following clauses:

Clause 1: A coupler including a first connector having a first end, a second end opposite the first end, and a first valve disposed between the first end and the second end. The first valve has a compressed state and an expanded state. The coupler also includes a second connector having a housing, a connecting portion extending from the housing, and a second valve disposed at least partially within the housing. The second valve has a compressed state and an expanded state. The coupler also includes a collar coupled to the housing of the second connector and configured to receive at least a portion of the first connector to detachably couple the first connector to the collar and the second connector such that the housing of the second connector extends through the first end of the first connector. The first valve and the second valve are in the compressed state when the first connector is coupled to the collar and the collar is coupled to the second connector. The first connector is configured to decouple from the collar and the second connector in response to a pullout force exceeding a predetermined threshold force.

Clause 2: The coupler of clause 1, wherein the collar includes a first collar end and second collar end opposite the first end, the first collar end including an engaging edge extending radially inward from the first collar end and a securing rim disposed at the second collar end.

Clause 3: The coupler of clause 2, wherein the first connector is coupled to the first collar end of the collar and the second connector is coupled to the second collar end when the first connector is coupled to the collar and the collar is coupled to the second connector.

Clause 4: The coupler of clause 2, wherein the engaging edge engages with a groove disposed on the second end of the first connector to secure the first connector to the collar when the first connector is coupled to the collar.

Clause 5: The coupler of clause 1, wherein the pullout force is a force applied to the first connector along a central axis of the first connector and the central axis extends at least along a length of the first connector.

Clause 6: The coupler of clause 5, wherein the central axis extends through the first connector, the collar, and the second connector when the first connector is coupled to the collar and the collar is coupled to the second connector.

Clause 7: The coupler of clause 1, wherein the first connector includes a body configured to compress the second valve when the first connector is coupled to the collar and the collar is coupled to the second connector.

Clause 8: The coupler of clause 7, wherein the body is at least partially disposed within the housing when the first connector is coupled to the collar and the collar is coupled to the second connector.

Clause 9: The coupler of clause 1, wherein the second valve is in the expanded state when the first connector is disconnected from the collar.

Clause 10: The coupler of clause 1, wherein the first valve is in the expanded state when the first connector is disconnected from the collar.

Clause 11: The coupler of clause 1, wherein the first connector is configured to remain coupled to the collar when the pullout force does not exceed the predetermined threshold force.

Clause 12: The coupler of clause 1, wherein the first valve does not overlap with the second valve.

Clause 13: The coupler of clause 1, wherein at least a portion of the housing is configured to compress the first valve when the first connector is coupled to the collar and the collar is coupled to the second connector.

Clause 14: The coupler of clause 1, wherein the coupler has a first configuration and in the first configuration the first connector coupled to the collar and the collar is coupled to the second connector such that the first connector is at least partially disposed within the collar and the second connector is at least partially disposed within the first connector.

Clause 15: The coupler of clause 1, wherein the coupler has a second configuration and in the second configuration the first connector is disconnected from the collar and the collar is coupled to the second connector.

Clause 16: The coupler of clause 1, wherein the first connector is coupled to a first portion of tubing at the first end and the second connector is coupled to a second portion of tubing at the connecting portion.

Clause 17: The coupler of clause 1, wherein the second connector includes a distributor and a channel having an inlet, the second valve being coupled to the distributor and the distributor is disposed between the inlet and an opening of the housing.

Clause 18: The coupler of clause 1, wherein a fluid pathway is formed between the connecting portion of the second connector and the first end of the first connector when the first connector is coupled to the collar and the collar is coupled to the second connector.

Clause 19: A coupler including a first connector having a first end, a second end opposite the first end, a body having a channel, and a first valve disposed between the first end and the second end. The first valve has a compressed state and an expanded state. The coupler also includes a second connector having a housing, a connecting portion extending from the housing, and a second valve disposed at least partially within the housing. The second valve has a compressed state and an expanded state and the housing having an opening configured to receive a portion of the first connector. The coupler also includes a collar coupled to the housing of the second connector and configured to receive at least a portion of the first connector to detachably couple the first connector to the collar and the second connector such that the housing of the second connector extends through the first end of the first connector. The collar has a first collar end and second collar end opposite the first end, the first collar end including an engaging edge extending radially inward from the first collar end and a securing rim disposed at the second collar end. The first valve and the second valve are in the compressed state when the first connector is coupled to the collar. The first connector is configured to decouple from the collar and the second connector in response to a pullout force exceeding a predetermined threshold force.

Clause 20: A coupler including a first connector having a first end, a second end opposite the first end and including a groove, a body having a channel and a fluid opening, and a first valve disposed between the first end and the second end. The first valve has a compressed state and an expanded state. The fluid opening is fluid communication with the channel. The coupler also includes a second connector having a housing, a connecting portion extending from the housing, and a second valve disposed at least partially within the housing. The second valve has a compressed state and an expanded state. The housing has an opening configured to receive a portion of the first connector. The second valve seals the opening when second valve is in the expanded state. The coupler also includes a collar coupled to the housing of the second connector and configured to receive at least a portion of the first connector to detachably couple the first connector to the collar and the second connector such that the housing of the second connector extends through the first end of the first connector. The collar has a first collar end and second collar end opposite the first end. The first collar end includes an engaging edge extending radially inward from the first collar end and a securing rim disposed at the second collar end. The engaging edge is disposed within the groove when the first connector is coupled to the collar. The first valve and the second valve are in the compressed state when the first connector is coupled to the collar. The first connector is configured to decouple from the collar and the second connector in response to a pullout force exceeding a predetermined threshold force. A fluid pathway is formed between the first end of the first connector and the connecting portion of the second connector and when the first connector is coupled to the collar and the collar is coupled to the second connector.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A coupler comprising:
a first connector having a first end, a second end opposite the first end, a body, a mating portion, a groove disposed on the mating portion, and a first valve disposed longitudinally between the first end and the second end and radially between the body and the mating portion, the first valve having a compressed state and an expanded state;
a second connector having a housing, a connecting portion extending from the housing, and a second valve disposed at least partially within the housing, the second valve having a compressed state and an expanded state; and
a collar coupled to the housing of the second connector and comprising an engaging edge configured to engage with the groove to detachably couple the first connector to the collar and the second connector such that the housing of the second connector extends through the first end of the first connector,
wherein the first valve and the second valve are in the compressed state when the first connector is coupled to the collar and the collar is coupled to the second connector,
wherein the first connector is configured to decouple from the collar and the second connector in response to a pullout force exceeding a predetermined threshold force and displacing the engaging edge from the groove.

2. The coupler of claim 1, wherein the collar includes a first collar end, a second collar end opposite the first collar end, and a securing rim disposed at the second collar end, the engaging edge extending radially inward from the first collar end.

3. The coupler of claim 2, wherein the first connector is coupled to the first collar end of the collar and the second connector is coupled to the second collar end when the first connector is coupled to the collar and the collar is coupled to the second connector.

4. The coupler of claim 1, wherein the pullout force is a force applied to the first connector along a central axis of the first connector and the central axis extends at least along a length of the first connector.

5. The coupler of claim 4, wherein the central axis extends through the first connector, the collar, and the second connector when the first connector is coupled to the collar and the collar is coupled to the second connector.

6. The coupler of claim 1, wherein body is configured to compress the second valve when the first connector is coupled to the collar and the collar is coupled to the second connector.

7. The coupler of claim 1, wherein the body is at least partially disposed within the housing when the first connector is coupled to the collar and the collar is coupled to the second connector.

8. The coupler of claim 1, wherein the second valve is in the expanded state when the first connector is disconnected from the collar.

9. The coupler of claim 1, wherein the first valve is in the expanded state when the first connector is disconnected from the collar.

10. The coupler of claim 1, wherein the first connector is configured to remain coupled to the collar when the pullout force does not exceed the predetermined threshold force.

11. The coupler of claim 1, wherein the first valve does not overlap with the second valve.

12. The coupler of claim 1, wherein at least a portion of the housing is configured to compress the first valve when the first connector is coupled to the collar and the collar is coupled to the second connector.

13. The coupler of claim 1, wherein the coupler has a first configuration and in the first configuration the first connector coupled to the collar and the collar is coupled to the second connector such that the first connector is at least partially disposed within the collar and the second connector is at least partially disposed within the first connector.

14. The coupler of claim 1, wherein the coupler has a second configuration and in the second configuration the first connector is disconnected from the collar and the collar is coupled to the second connector.

15. The coupler of claim 1, wherein the first connector is coupled to a first portion of tubing at the first end and the second connector is coupled to a second portion of tubing at the connecting portion.

16. The coupler of claim 1, wherein the second connector includes a distributor and a channel having an inlet, the second valve being coupled to the distributor and the distributor is disposed between the inlet and an opening of the housing.

17. The coupler of claim 1, wherein a fluid pathway is formed between the connecting portion of the second connector and the first end of the first connector when the first connector is coupled to the collar and the collar is coupled to the second connector.

18. A coupler comprising:

a first connector having a first end, a second end opposite the first end, a body having a channel, a mating portion, a groove disposed on the mating portion, and a first valve disposed longitudinally between the first end and the second end and radially between the body and the mating portion, the first valve having a compressed state and an expanded state;

a second connector having a housing, a connecting portion extending from the housing, and a second valve disposed at least partially within the housing, the second valve having a compressed state and an expanded state and the housing having an opening configured to receive a portion of the first connector; and a collar coupled to the housing of the second connector and configured to receive at least a portion of the first connector to detachably couple the first connector to the collar and the second connector such that the housing of the second connector extends through the first end of the first connector, the collar having a first collar end and second collar end opposite the first end, the first collar end including an engaging edge extending radially inward from the first collar end and a securing rim disposed at the second collar end, wherein the first valve and the second valve are in the compressed state when the engaging edge engages with the groove, wherein the first connector is configured to decouple from the collar and the second connector in response to a pullout force exceeding a predetermined threshold force.

19. A coupler comprising:

a first connector having a first end, a second end opposite the first end, a mating portion with a groove, a body having a channel and a fluid opening, and a first valve disposed longitudinally between the first end and the second end and radially between the groove and the body, the first valve having a compressed state and an expanded state, wherein the fluid opening is fluid communication with the channel;

a second connector having a housing, a connecting portion extending from the housing, and a second valve disposed at least partially within the housing, the second valve having a compressed state and an expanded state and the housing having an opening configured to receive a portion of the first connector, wherein the second valve seals the opening when second valve is in the expanded state; and a collar coupled to the housing of the second connector and configured to receive at least a portion of the first connector to detachably couple the first connector to the collar and the second connector such that the housing of the second connector extends through the first end of the first connector, the collar having a first collar end and second collar end opposite the first end, the first collar end including an engaging edge extending radially inward from the first collar end and a securing rim disposed at the second collar end, the engaging edge disposed within the groove when the first connector is coupled to the collar, wherein the first valve and the second valve are in the compressed state when the first connector is coupled to the collar, wherein the first connector is configured to decouple from the collar and the second connector in response to a pullout force exceeding a predetermined threshold force, wherein a fluid pathway is formed between the first end of the first connector and the connecting portion of the second connector and when the first connector is coupled to the collar and the collar is coupled to the second connector.

* * * * *